June 9, 1959 H. J. WILLIAMS Plant Pat. 1,839

PEACH TREE

Filed Oct. 20, 1958

WITNESS

Addison E Avery

INVENTOR

Horace J. Williams

Webster & Webster

ATTYS.

United States Patent Office

Plant Pat. 1,839

Patented June 9, 1959

1,839

PEACH TREE

Horace J. Williams, Porterville, Calif., assignor to Williams & Sons, Inc., Porterville, Calif., a corporation of California Application October 20, 1958, Serial No. 768,504

1 Claim. (Cl. 47—62)

This discovery relates to a new and distinct variety of peach tree which bears large freestone fruit having yellow flesh mottled and streaked with red outwardly from the stone, and yellow skin blushed with red.

The present variety of peach tree is a bud sport of the Rio Oso Gem (United States Plant Patent No. 84), and there is general similarity in the tree, its productiveness, and the size, color, and quality of the fruit; the distinguishing characteristic being a ripening period which is later by approximately two weeks.

The first picking of the fruit of the present variety of peach tree begins shortly after the last picking of the Rio Oso Gem; thus desirably extending the market season for the fruit of the type described.

The peach tree herein claimed was discovered by me as a sport limb on a mature Rio Oso Gem peach tree in my orchard located near Porterville, California; such sport limb having first been noticed because the fruit was not ripe and did not ripen until after the last picking of the fruit on other limbs of such tree.

Such sport limb—under careful observation by me—was checked at maturity and marked so that it could be subsequently identified. Thereafter, bud wood was obtained from the sport limb for June budding the following year; such June budding having been made on peach seedlings—for my account, and under my direction—by a commercial nursery located at Merced, California.

The June budded seedlings were then transplanted to—and grown under careful observation in an orchard located near Porterville, California.

When such asexual reproductions of the variety grew to maturity and bore fruit they were found to remain true to the parent in all respects.

Figure 1:
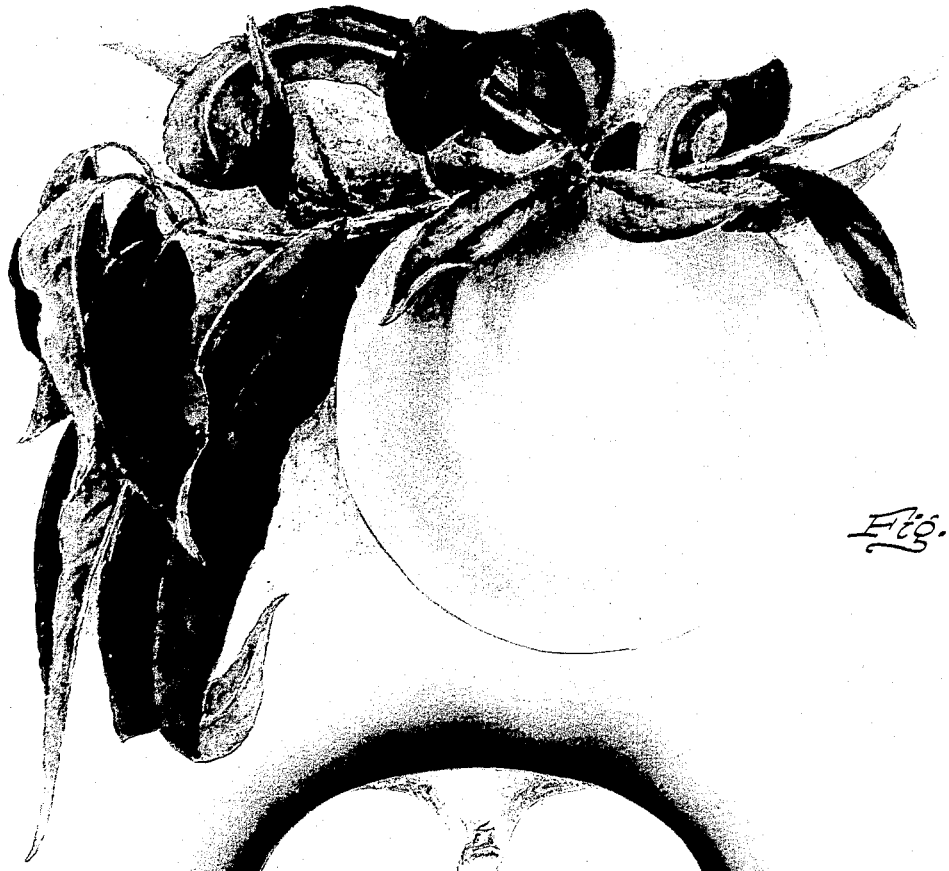
Fig. 1 is an elevation of one of the fruit, together with twigs and leaves.
Figure 2:
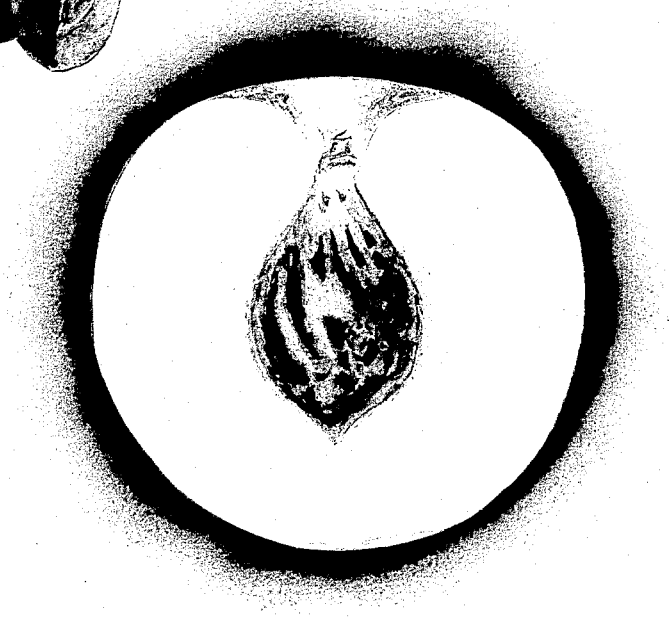
Fig. 2 is a sectional elevation of one of the fruit, with the stone exposed.

All major plate identifications in the following specification are by reference to Maerz and Paul Dictionary of Color, except where common terms of color definition are employed.

The present variety of peach tree is—as aforesaid—generally similar to the Rio Oso Gem in tree and fruit characteristics, and the following outline description of the leaves, flowers, and fruit will serve for the purpose of more precise identification:

Leaves:

*Size.*—Medium. Average length—6¾″ to 7¾″. Average width—1¼″ to 1⅝″.

*Form.*—Lanceolate, occasionally oval-lanceolate.

*Apex.*—Acute; acuminate.

*Base.*—Acute.

*Margin.*—Finely serrate; broadly sinuate.

*Blade.*—Flat or somewhat folded; thin; pliable.

*Petiole.*—Moderately stout; distinctly channeled on ventral side. Average length—5/16″ to 7/16″.

*Stipules.*—Dehiscent.

*Glands.*—Medium to small size. Average number—two, occasionally three or four. Borne apically on the petiole or just at the base of the heads.

*Shoots.*—Strong. Green, becoming brownish, with longitudinal, light brown striations with diameter increase.

*Foliage buds.*—Small; conic; brown with greyish pubescence; appressed.

*Color.*—Top side—medium green (22–L–8). Under side—lighter green (21–L–7).

Flower buds: Uusually two per znode, lateral to the foliage buds. Round conic; medium size; usually distinctly larger than the foliage buds; appressed. Color—same as foliage buds.

Flowers: Large; pink; showy.

Fruit:

*Maturity when described.*—Eating ripe.

*Date of first picking in average season.*—August 26th.

*Date of last picking in average season.*—September 5th.

*Size.*—Large. Average length (axial diameter—2⅝″ to 2⅞″. Average cheek diameter—2⅞″ to 3⅛″. Average suture diameter—2¾″ to 3″.

*Form.*—Somewhat variable. Round-truncate, occasionally round-oblate or round-ovate to short oblong in cheek aspect; round-truncate to round-ovate in suture aspect. In cheek aspect the ventral suture markedly longer than the dorsal. Halves equal or nearly so.

*Base.*—Short oval to round; shoulders rounded; regular; often creased at ventral suture. Broadly, shallowly depressed to medium depth opposite. Average width—1¼″ to 1 3/16″. Average depth—½″.

*Apex.*—Flat to rounded, or often slightly mamelonated.

*Suture.*—Broadly protruding; more or less roughened from near base to near apex; often creased at basal cavity; often lightly depressed ventral to apical scar; broadly but shallowly depressed dorsally next to apical scar; often obscurely grooved along the dorsal edge to the base; lips rounded; ventral suture frequently with darker overcolor than adjoining surface.

Skin:

*Pubescence.*—Moderate.

*Thickness.*—Thin.

*Toughness.*—Tender.

*Color.*—Yellow (9–L–3 shading to 10–L–8), blushed with red (4–K–5 shading to darker 7–L–6).

Flesh:

*Texture.*—Firm; melting; fine grained.

*Fibers.*—Few; soft.

*Flavor.*—Subacid; mild; moderately sweet; very good.

*Color.*—Yellow (9–L–4 shading to 9–L–6), mottled and streaked with red (3–K–5) outwardly from the stone cavity. Surface of pit cavity—bright red.

Stone:

*Type.*—Free.

*Size.*—Medium, or less. Average length (axial)—1 3/16″ to 1 7/16″. Average cheek diameter—⅝″ to ¾″. Average suture diameter—15/16″ to 1″.

*Form.*—Round to long oval.

*Surface.*—Deeply and irregularly furrowed and pitted.

*Ridges.*—Rounded or rarely sharp.

*Ventral suture.*—Narrow. Finely ridged toward base, otherwise not raised. Irregularly erroded, with deep narrow grooves close on either side.

*Dorsal suture.*—Slightly raised; narrow; grooved from base to near apex; margins interrupted.

*Apex.*—Blunt point of medium length; dorsal or ventral edge often recurved at apex.

*Stem scar.*—Moderate size; oval.

*Color.*—Deep brown (8–H–6), usually stained red near base and along ventral suture.

Use: Market; dessert.

Keeping quality: Good.

Shiping quality: Good.

I claim:

A new and distinct variety of peach tree, as illustrated and described, which bears large freestone fruit having yellow flesh mottled and streaked with red outwardly from the stone, and yellow skin blushed with red, characterized—in comparison with the Rio Oso Gem—by general similarity of tree and fruit, but having a ripening period approximately two weeks later; such fruit having a first picking subsequent to the last picking of said Rio Oso Gem.

No references cited.